US00PP17025P3

(12) United States Plant Patent
Danziger

(10) Patent No.: US PP17,025 P3
(45) Date of Patent: Aug. 22, 2006

(54) ***TORENIA* PLANT NAMED 'DANCATPINK'**

(50) Latin Name: ***Torenia* sp.**
Varietal Denomination: Dancatpink

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 25 days.

(21) Appl. No.: 10/929,434

(22) Filed: Aug. 31, 2004

(65) Prior Publication Data

US 2006/0048252 P1 Mar. 2, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Louanne Krawczewicz Myers
(74) *Attorney, Agent, or Firm*—Foley & Lardner LLP

(57) ABSTRACT

A new and distinct *Torenia* plant named 'Dancatpink' characterized by delicate, funnel form flowers consisting of four petals in which the top petal is pale purple, RHS 76B, and the lower and side petals are purple, RHS 77A, with a yellow-green blotch in the center of the lower petal, RHS 154A; its vigorous growth habit, its bushy and cascading growth habit which maintains its compact rounded growth; its dense branching which gracefully cascades from hanging baskets; its early flowering response and year round blooming in a moderate climate; its suitability as an annual for hanging pots outdoors under partial shade; and its good weather tolerance.

2 Drawing Sheets

Latin name of the genus and species of the plant claimed: *Torenia* sp.
Variety denomination: 'Dancatpink'.

BACKGROUND OF THE INVENTION

The present invention relates to a new and distinct cultivar of *Torenia* plant, botanically known as *Torenia* sp. of the Scrophulariaceae family, hereinafter referred to by the cultivar name 'Dancatpink'.

'Dancatpink' was discovered and selected by the inventor, Gabriel Danziger, as a flowering plant in a controlled environment in Moshav Mishmar Hashiva, Israel.

'Dancatpink' is an induced mutant of the cultivar *Torenia* sp. 'Rose Moon' (unpatented) selected in a cultivated environment in Moshav Mishmar Hashiva, Israel. The mutation arose by radiation,stabilized by removing the cutting from the mutated sector of the treated plant.

Asexual reproduction of the new cultivar by soft tip cuttings was first performed in May, 2002 in Moshav Mishmar Hashiva, Israel, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'Dancatpink' which in combination distinguish this *Torenia* as a new and distinct cultivar:

1. Delicate, funnel form flowers consisting of four petals in which the top petal is pale purple, RHS 76B, and the lower and side petals are purple, RHS 77A, with a yellow-green blotch in the center of the lower petal, RHS 154A;

2. Bushy, cascading growth habit, vigorous growth, maintains compact rounded growth;
3. Densely branched plant, gracefully cascading from hanging baskets;
4. Early flowering response and year round blooming in moderate climate;
5. Suitable as an annual for hanging pots outdoors under partial shade; and
6. Good weather tolerance.

Of the many commercial cultivars known to the inventor, the most similar in comparison to 'Dancatpink' is the parental cultivar *Torenia* sp. 'Rose Moon' (unpatented) as described in Table 1.

TABLE 1

| Characteristic | *Torenia* sp. 'Dancatpink' | *Torenia* sp. 'Rose Moon' (unpatented) |
|---|---|---|
| Flower color | The upper petal is pale purple, and the lower and side petals are purple, with a yellow-green blotch in the center of the lower petal. | Light Red-Purple |
| Flower size (cm) | Depth: 3 cm<br>Width: 3 cm | Depth: 3.1 cm<br>Width: 3 cm |
| Growth habit | Bush, cascading | Bush, cascading |
| Flowering time | 8 weeks from planting | 8 weeks from planting |

'Dancatpink' has not been observed under all possible environmental conditions. The phenotype of the new cultivar may vary significantly with variations in environment such as temperature, light intensity, and day length without any change in the genotype of the plant. The following observations, measurements and values describe the new cultivar as grown in Moshav Mishmar Hashiva, Israel under conditions, which closely approximate those generally used in commercial practice.

BRIEF DESCRIPTION OF THE DRAWINGS

The accompanying photographic drawings show typical flower and foliage characteristics of 'Dancatpink' with colors being as true as possible with illustrations of this type.

The first photograph shows a full flowering plant of 'Dancatpink' in its entirety in a hanging basket.

The second photograph shows a close-up of 'Dancatpink' flowers showing the intense red-purple and pale purple flower color with yellow base on central lobe.

DETAILED BOTANICAL DESCRIPTION

The following observations, measurements and values describe the new cultivar as grown in Moshav Mishmar Hashiva, Israel under conditions, which closely approximate those generally used in commercial practice. Optimally, 'Dancatpink' is used as a pot plant, grown outdoors in moderate climate, indoors during winter. Irrigation and fertilization is recommended on a regular basis. 'Dancatpink' is best grown in full sunlight; partial shade is required in mid summer. A fully grown 'Dancatpink' plant takes 3 months. 'Dancatpink' blooms year-round in moderate climate.

Color references are made to The Royal Horticultural Society Color Chart (R.H.S.), except where general colors of ordinary significance are used. Color values were taken under daylight conditions at approximately noon in Moshav Mishmar Hashiva, Israel.

The age of the plants described is 3 months. The 'Dancatpink' plants described were grown indoors in 16 cm pots in a glass greenhouse in Moshav Mishmar Hashiva, Israel, with the day temperatures ranging from 18° C. to 35° C. and night temperatures ranging from 16° C. to 25° C. Plants of 'Dancatpink' were fertilized up to a level of 59 ppm N, 35.4 ppm P and 94.4 ppm K.

Propagation: Tissue culture and soft tip cuttings.

Plant:

*Form.*—Bush cascading.

*Growth habit.*—Compact, rounded.

*Height.*—10 cm.

*Spread.*—60–80 cm.

*Blooming period.*—Year round in moderate climate.

*Cold tolerance.*—Frost tender, plants may be damaged by temperatures below 5° C.

*Vigor.*—Vigorous growth; plants are fully grown in 3 months from planting a cutting in summer season.

Stem:

*Color.*—Green, RHS 143-A.

*Length.*—Up to 40 cm.

*Diameter.*—2 mm.

*Pubescence.*—Minimal.

*Branching.*—Between 5 and 10 main branches grow from the base and split into hundreds of secondary branches.

*Length of internodes.*—3–4 cm.

Foliage:

*Overall shape.*—Obovate.

*Base.*—Triangular, cordate base.

*Tip.*—Acuminate.

*Margin.*—Serrate.

*Color.*—Center color of leaf: Green, RHS 137-A. Upper side: Green, RHS 137-A. Under side: Yellow-Green, RHS 146-B.

*Size of leaf.*—Width: 3.0 cm. Length: 3.5 cm.

*Texture*: Smooth, few hairs.

*Venation.*—Not prominent. Pattern: Anastomotic; midrib splits to 4–6 secondary veins. Color: Upper surface: Green, RHS 137-A. Lower surface: Yellow-Green, RHS 146-B.

*Petioles.*—Length: 5–7 mm. Width: 3 mm. Color: Yellow-Green, RHS 146-B.

Flowers:

*Blooming period.*—Typical: Year round in moderate climate; Observed: February to November in Moshav Mishmar Hashiva, Israel.

*Time for plant to produce flowers.*—About 3 weeks from planting cutting in summer season.

*Quantity of flowers.*—Per lateral stem: About 4 to 6; Per plant: About 230 to 250.

*Flowering stem.*—Flowers appear along the growing stems.

*Flower longevity on the plant.*—About 9 months.

*Lastingness of the individual bloom* (*vase life*).—About 2–5 days.

*Fragrance.*—None.

*Orientation at opening.*—Slanted upward.

*Type.*—Single.

*Shape.*—Overall: Funnel-form; 5-winged; Corolla tube: cylindrical or often broadened above; Corolla: 2-lipped, the upper lip faintly 2-lobed, the lower lip 3-lobed.

*Flower size.*—Depth: About 3 cm. Width: About 3 cm.

*Petals.*—Number: Four and fused. Petal Size: Length: Upper: About 2.8 cm; Sides: About 1.5 cm; Lower: About 1.8 cm. Width: Upper: About 1.5 cm; Sides: About 1.1 cm; Lower: About 1.4 cm. Shape: Upper: Overall: orbicular, Apex: rounded, Base: fused; Sides: Overall: spatulate, Apex: rounded, Base: fused; Lower: Overall: spatulate, Apex: rounded, Base: fused. Margin: Entire and undulated. Color: Four petals in which the upper petal is pale purple, and the lower and side petals are purple, with a yellow-green blotch in the center of the lower petal. Mature: Upper side: Upper petal: light purple, RHS 76B; Lower and side petals: purple, RHS 77A, with yellow-green blotch in the middle of the lower petal, RHS 154A. Under side: Upper petal: light purple, RHS 76B; Lower and side petals: purple, RHS 77B. Margin: Light purple, RHS 76B (same for upper and under side of mature petals). Throat: Purple, RHS 76B, to yellow-green, RHS 154A, the color changes when going down the throat. Immature: Upper side: Upper petal: light purple, RHS 76B; Lower and side petals: purple, RHS 77A, with yellow-green blotch in the middle of the lower petal, RHS 154A. Under side: Upper petal: light purple, RHS 76B; Lower and side petals: purple, RHS 77B. Margin: Purple, RHS 77A (same for upper and under side of immature petals). Throat: Purple, RHS 76B, to yellow-green, RHS 154A, the color changes when going down the throat.

*Floral tube.*—Length: Typical: About 3.5 cm; Observed: About 3.5 cm. Width: Typical: About 3 cm; Observed: About 3 cm. Color: Outside: Purple, RHS 76B, to yellow-green, RHS 154A, to Purple, RHS 77A (color changes when going down the tube); Inside: Purple, RHS 76B, to yellow-green, RHS 154A (color changes when going down the tube).

*Sepals.*—Number: 5. Length: About 2 cm. Width: About 0.5 cm. Shape: Two-lobed, 5 winged. Apex:

Acute. Base: Wedge shaped. Margin: Undulated. Color: Yellow-Green, RHS 144A.

*Peduncle.*—Diameter: About 2 mm. Length: 2 cm. Texture: Few hairs on edges of the peduncle. Color: Green, RHS 143-B.

*Bud.*—Shape: Oblong, cylindrical, ellipsoid, 5 winged. Size: Length: About 25 mm. Diameter: About 10 mm. Color: Apex, purple, RHS 77A, base, green, RHS 143B. Texture: Pubescence on winged edges.

Reproductive organs:

*Androecium.*—Stamen: Number: 2 pairs per flower, fused. Color: Violet-blue, RHS 92 D. Anther: Length: About 0.4 cm; upper anthers shorter — about 0.3 cm. Width: About 1.0 mm. Color: Violet-Blue, RHS 92 B. Spur: Present. Filament: Length: About 1.3 cm; lower filaments shorter — about 0.5 cm. Width: About 5 mm. Color: Violet-Blue, RHS 92 D. Pollen: Amount: Sparse. Color: White, RHS N155B. Requirements: Young flowers, vital pollen, and receptive, open stigma.

*Gynoecium.*—Pistil: Number: One per flower. Length: About 2.4 cm. Stigma: Shape: Two lobes, open to opposite side, deltoid shape. Length: About 0.2 cm. Width: About 0.2 cm. Color: Violet-Blue, RHS 92D. Style: Length: About 2 cm. Color: Violet-Blue, RHS 92 D. Ovary: Number: 1. Length: About 5 mm. Width: About 2 mm. Color: Green, RHS 143-B.

Seed/fruit: None.

Pest/disease resistance and/or susceptibility: A standard preventative spray program is sufficient as no susceptibility was observed.

I claim:

1. A new and distinct *Torenia* plant named 'Dancatpink', as illustrated and described herein.

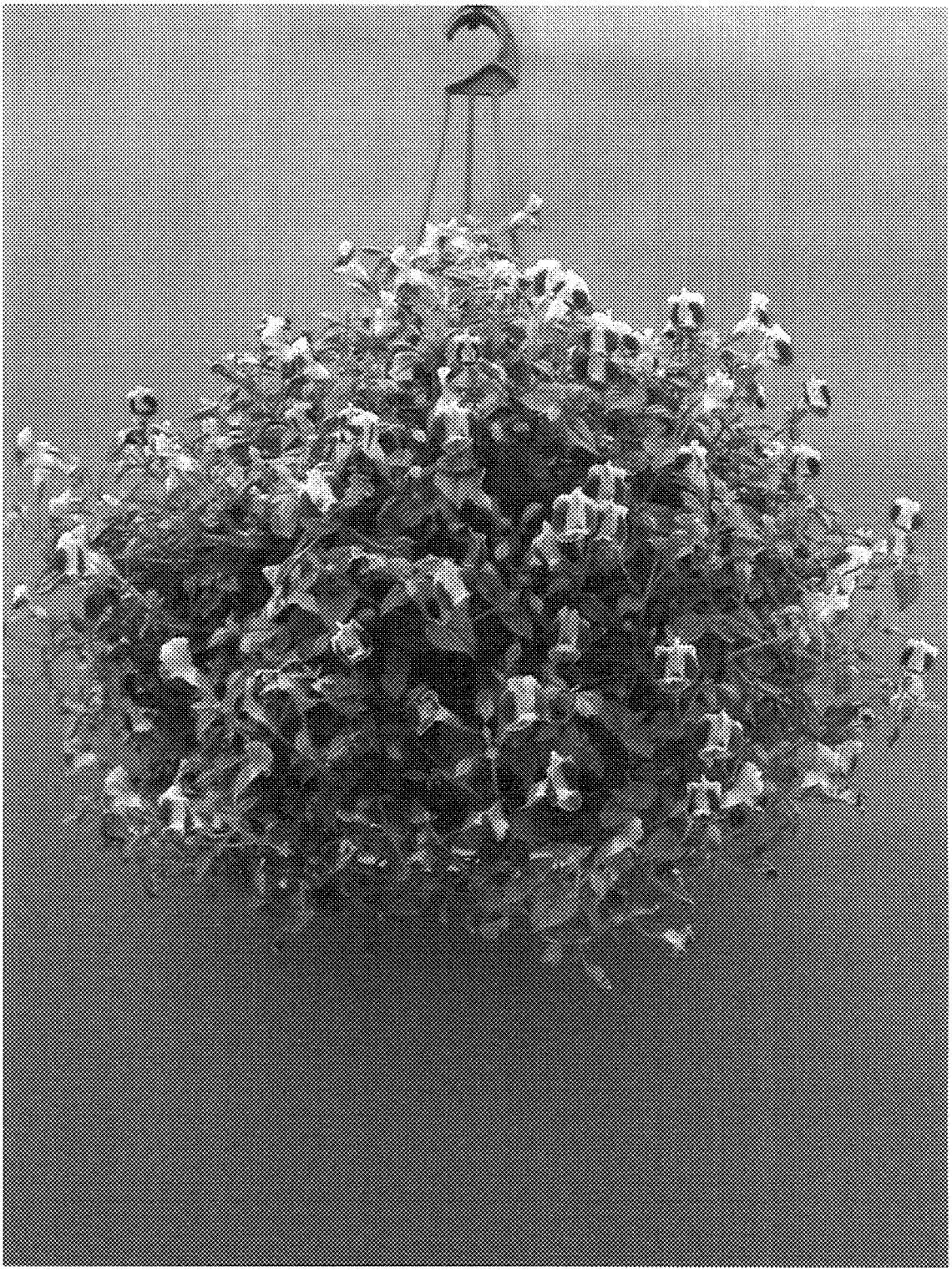

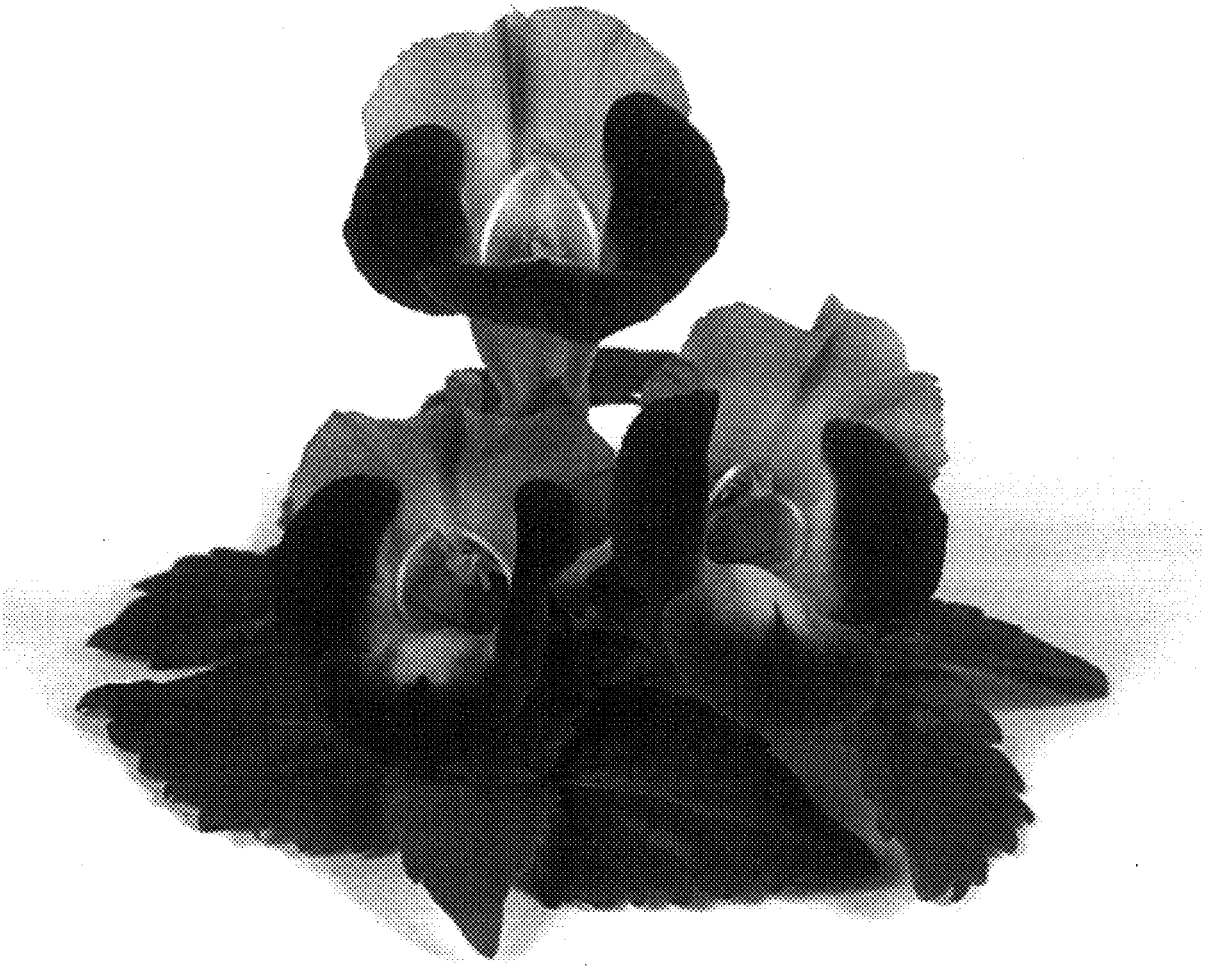

* * * * *